(12) United States Patent
Lenna et al.

(10) Patent No.: US 9,422,326 B2
(45) Date of Patent: Aug. 23, 2016

(54) PROCESS FOR PREPARING 11-METHYLENE-18-METHYL-ESTR-4-EN-3, 17-DIONE, USEFUL AS INTERMEDIATE COMPOUND FOR THE SYNTHESIS OF MOLECULES HAVING PHARMACOLOGICAL ACTIVITY

(71) Applicant: Industriale Chimica S.r.l., Milan (IT)

(72) Inventors: Roberto Lenna, S. Giorgio su Legnano (IT); Edoardo Mariani, Santa Maria del Taro (IT); Andrea Vanossi, Merone (IT)

(73) Assignee: INDUSTRIALE CHIMICA S.r.l. (IT)

( * ) Notice: Subject to any disclaimer, the term of this patent is extended or adjusted under 35 U.S.C. 154(b) by 0 days.

(21) Appl. No.: 14/423,783

(22) PCT Filed: Sep. 3, 2013

(86) PCT No.: PCT/IB2013/058248
§ 371 (c)(1),
(2) Date: Feb. 25, 2015

(87) PCT Pub. No.: WO2014/037873
PCT Pub. Date: Mar. 13, 2014

(65) Prior Publication Data
US 2015/0239925 A1    Aug. 27, 2015

(30) Foreign Application Priority Data
Sep. 4, 2012   (IT) .............................. MI2012A1472

(51) Int. Cl.
C07J 21/00    (2006.01)
C07J 1/00    (2006.01)
(52) U.S. Cl.
CPC ................ *C07J 21/006* (2013.01); *C07J 1/007* (2013.01); *C07J 1/0059* (2013.01)

(58) Field of Classification Search
CPC ...................................... C07J 21/006
See application file for complete search history.

(56) References Cited

U.S. PATENT DOCUMENTS 3,927,046 A    12/1975   van den Broek

FOREIGN PATENT DOCUMENTS

CN            1865276 A      11/2006
WO        2008039566 A2      4/2008

OTHER PUBLICATIONS

Gao, H. et al., "An improved synthesis of 13[beta]-ethyl-11-methylenegon-4-en-3,17-dione", Synthetic Communications, 1997, vol. 27, No. 11, pp. 1981-1987, US.
Gao, H. et al., "Sythesis of 13-ethyl-11-methylene-18, 19-dinor-17α-pregn-4-en-20-yn-17-ol", Oppi Briefs, 1997, vol. 29, No. 5, pp. 572-576.

*Primary Examiner* — Brian McDowell
(74) *Attorney, Agent, or Firm* — Fish & Tsang, LLP

(57) ABSTRACT

There is described a process for the industrial synthesis of 11-methylene-18-methyl-estr-4-en-3,17-dione, a compound having the structure formula (I) depicted below: (Formula I) (I) useful as intermediate compound in the synthesis of the progestin compounds Desogestrel and Etonogestrel.

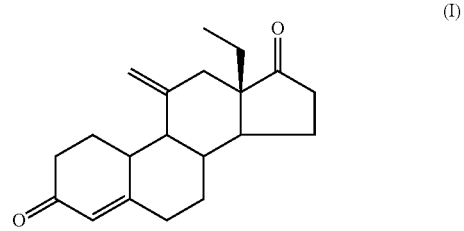

3 Claims, No Drawings

PROCESS FOR PREPARING 11-METHYLENE-18-METHYL-ESTR-4-EN-3, 17-DIONE, USEFUL AS INTERMEDIATE COMPOUND FOR THE SYNTHESIS OF MOLECULES HAVING PHARMACOLOGICAL ACTIVITY

FIELD OF THE INVENTION

The present invention relates to a process for the industrial synthesis of 11-methylene-18-methyl-estr-4-en-3,17-dione, a compound having the structure formula (I) depicted below:

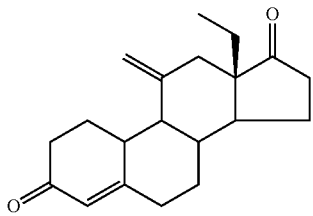
(I)

Compound 11-methylene-18-methyl-estr-4-en-3,17-dione is an intermediate compound useful in the synthesis of the progestin compounds (17α),13-ethyl-11-methylene-18,19-dinorpregna-4-en-20-yn-17β-ol and (17α),13-ethyl-17-hydroxy-11-methylene-18,19-dinorpregna-4-en-20-yn-3-one, known in the field as Desogestrel and Etonogestrel, respectively, having the structure formulas depicted below:

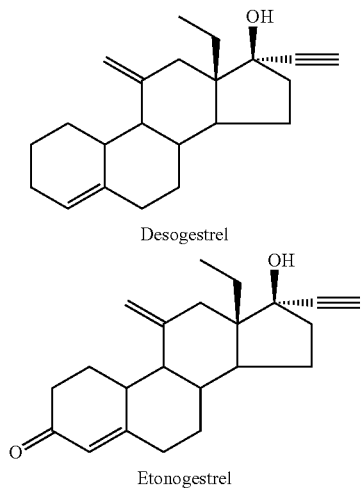

Desogestrel

Etonogestrel

BACKGROUND ART

Desogestrel and Etonogestrel are used in third-generation contraceptive formulations particularly useful for the administration to subjects suffering from diabetes or lipid disorder, due to their minimal impact on glucose levels in blood and lipid profile. Furthermore, Desogestrel and Etonogestrel can be used at lower estrogen doses than second-generation contraceptives, reducing the likelihood of weight increase, mastodynia and migraine.

The synthesis of Desogestrel and Etonogestrel is generally carried out from the intermediate compound 11-methylene-18-methyl-estr-4-en-3,17-dione having the above-depicted formula (I). For example, the preparation of Etonogestrel from compound (I) is described in article "Synthesis of 13-ethyl-17-hydroxy-11-methylene-18,19-dinor-17α-pregn-4-en-20-yn-3-one (3-oxo desogestrel)", H. Gao et al., STEROIDS, 1997, 62(5), 398-402; the synthesis of Desogestrel from compound (I) is described in article "A partial synthesis of 13-ethyl-11-methylene-18,19-dinor-17α-pregn-4-en-20-yn-17-ol (desogestrel) based upon intramolecular oxidation of an 11β-hydroxy-19-norsteroid to the 18→11β-lactone", M. J. van den Heuvel et al., Recueil des Travaux Chimiques des Pays-Bas, 107/4, 331-334 (1988).

The synthesis of 11-methylene-18-methyl-estr-4-en-3,17-dione is known from various patent and scientific literature documents.

The first document that describes the synthesis of compound (I) is U.S. Pat. No. 3,927,046 (1975). This synthesis uses 11α-hydroxy-18-methyl-estra-4-en-3,17-dione as starting product, which can be obtained from 3,17-diketo-18-methyl-estra-4-ene by hydroxylation in position 11α with *Aspergillus Ochraceus*; 11α-hydroxy-18-methyl-estra-4-en-3,17-dione is reacted with ethylene glycol, thus protecting the two ketone groups as acetals.

However, the synthesis described in this patent has some drawbacks.

Firstly, this synthesis results in a complex mixture of products due to both the migration of the double bond from positions 4(5) to positions 5(10) and 5(6), and to the configuration instability caused by the hydroxyl in 11α, as also noted in Tetrahedron 50(36), 10709-10720, 1994. This complex mixture of products, consisting of double bond isomers and of structural stereoisomers of the backbone, can be separated by sophisticated chromatography methods only with long and complex laboratory procedures, which makes this synthesis absolutely not applicable to prepare a product in such amounts to make it suitable for industrial development.

Another drawback of the synthesis in U.S. Pat. No. 3,927,046 is that among its steps, it comprises the oxidation of 11α-hydroxy-18-methylestr-5-en-3,17-dione-3,17-diethylene ketal to 18-methylestr-5-en-3,11,17-trione-3,17-diethylene ketal with the mixture $CrO_3$-sulfuric acid (Jones reagent); the use of a chromium reagent (VI), which is a recognized carcinogen, makes this synthesis not applicable to a large-scale production.

Finally, the methylene function in position 11 is introduced on 18-methylestr-5-en-3,11,17-trione-3,17-diethylene ketal through the triphenylphosphonium bromide ylide (Wittig reaction) and continues with the acid hydrolysis of the two acetals, thus obtaining the desired product; as an alternative, the oxidation of 11α-hydroxy-18-methyl-estra-4-en-3,17-dione to 18-methyl-estra-4-en-3,11,17-trione is carried out, followed by selective protection of carbonyls in position 3 and 17 as ketals. However, these methods do not have a synthetic utility at a practical level, as also noted in article "Selective Ketalization of Steroidal 3,11,17-Trione using Chlorotrimethylsilane as Catalyst", X. Su of al., Synthetic communications 25(18), 2807-2811 (1995).

On the other hand, also the preparation described in the same article by X. Su et al. also gives a 70% yield, with product recovery by silica gel chromatography at low pressure, and chromatography is a technique with a poor industrial utility as well.

Totally different syntheses, such as for example the one described in article "A short enantioselective total synthesis of the third-generation oral contraceptive Desogestrel", E. J. Corey et al., J. Am. Che. Soc. vol. 121(4) 710-714, 1999, where the steroid backbone is constructed, certainly have a scientific value but do not seem industrially applicable; a reason is that in order to obtain 17α-hydroxy-11-methylene-18-methylestr-4-en-3-one, at least 13 synthetic steps are required, which add up to the step required for the oxidation of position 17.

A similar drawback—the excessive number of reactions required—can also be found in the synthesis described in patent application CN 1865276 which, while starting from the steroid backbone already completed, requires 11 reaction steps to obtain 11-methylene-18-methylestr-4-en-3,17-dione.

SUMMARY OF THE INVENTION

It is the object of the present invention to obviate the drawbacks of the prior art processes.

In particular, it is the object of the invention to provide a process for the synthesis of 11-methylene-18-methylestr-4-en-3,17-dione, which avoids the use of chromium(VI)-based reagents, chromatographic purifications, and which reduces the overall number of reaction steps as compared to known processes.

These and other objects are achieved with the present invention which consists in a process for the synthesis of 11-methylene-18-methyl-estr-4-en-3,17-dione, comprising the following steps:

1) oxidation of 11α-hydroxy-18-methyl-estra-4-en-3,17-dione (II) to 18-methyl-estra-4-en-3,11,17-trione (III):

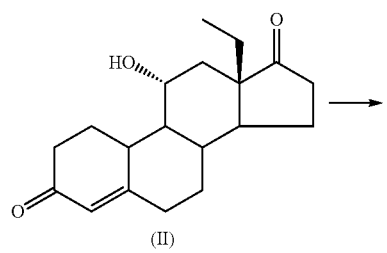

(II)

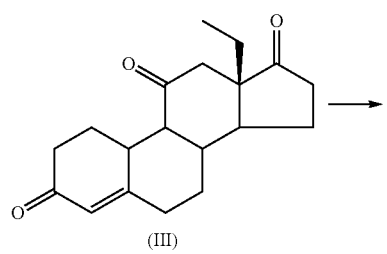

(III)

2) protection as acetal of position 3 of 18-methyl-estra-4-en-3,11,17-trione (III) to form 18-methyl-estr-5-en-3,11,17-trione 3,3'-acetal (IV):

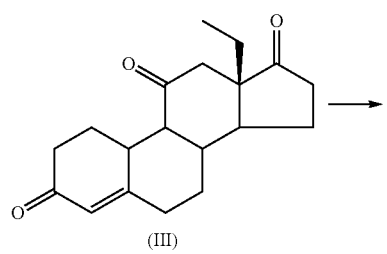

(III)

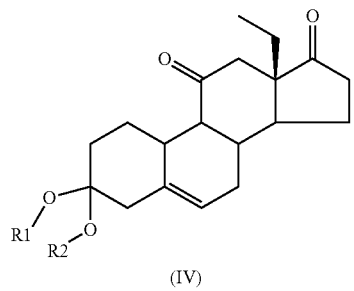

(IV)

3) selective reduction of the carbonyl group in position 17 of 18-methyl-estr-5-en-3,11,17-trione 3,3'-acetal (IV) to form 17-hydroxy-18-methyl-estr-5-en-3,11-dione 3,3'-acetal (V):

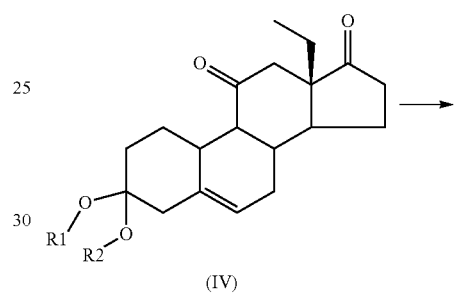

(IV)

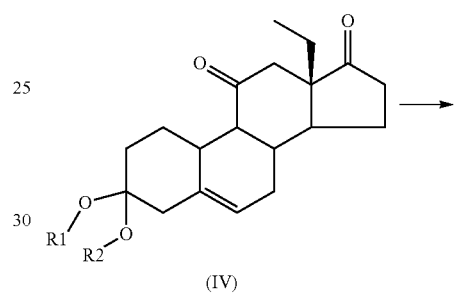

(V)

4) Wittig reaction on intermediate compound (V) to form the corresponding methylene derivative (VI), 17-hydroxy-11-methylene-18-methyl-estra-5-en-3-one-3,3' acetal:

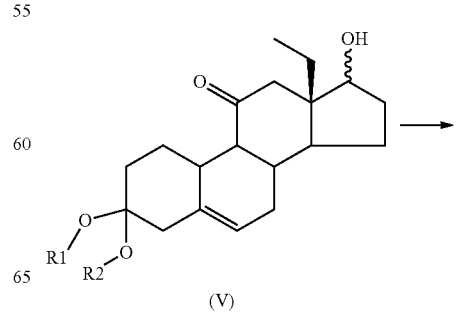

(V)

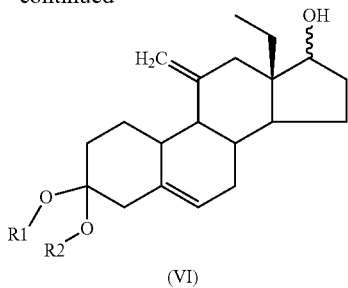

(VI)

5) oxidation of intermediate compound (VI) to form 11-methylene-18-methyl-estr-5-en-3,17-dione-3,3' acetal (VII):

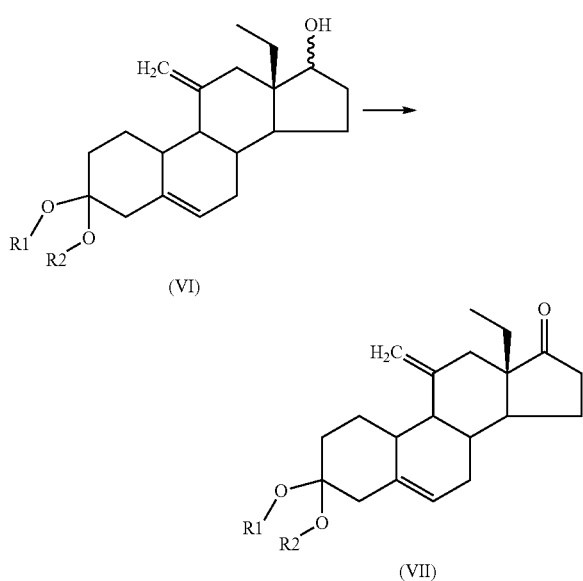

6) hydrolysis of intermediate compound (VII) to form 11-methylene-18-methyl-estr-4-en-3,17-dione (I):

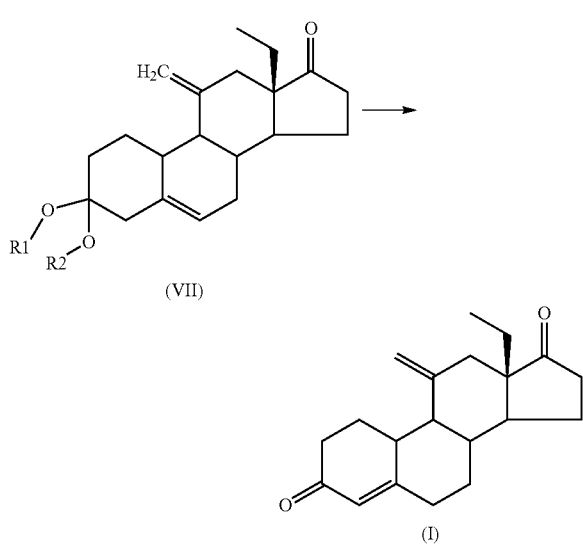

In the above formulas (IV)-(VII), R1 and R2 can be either separate alkyl radicals C1-C3 equal to each other, or they can form a unique bidentate alkyl radical C2-C4, thus forming a cyclic acetal structure; in formulas (V) and (VI), the symbol ⁓ indicates that the —OH group may have configuration α or β.

DETAILED DESCRIPTION OF THE INVENTION

The starting product of the synthesis of the invention is the same as the synthesis described in U.S. Pat. No. 3,927,046.

Reactions 1, 2 and 4 to 6 of the above-described synthesis are carried out with methods known to the man skilled in the art.

In particular, the oxidation of compound (II) (step 1) takes place by means of the complex pyridine-$SO_3$ in dimethylsulfoxide and in the presence of a tertiary amine; the protection of compound (III) (step 2) takes place by reacting the latter with the selected alcohol C1-C3 or glycol C2-C4 (preferred among the glycols are ethylene glycol or neopentyl glycol, 2,2-dimethyl-1,3-propandiol) in the presence of triethyl orthoformate and an acid; the Wittig reaction on compound (V) (step 4) takes place by treating this compound with a phosphonium salt (methyl triphenylphosphonium iodide is preferred) in the presence of a base such as an alkaline hydride or an alkoxide; the oxidation of compound (VI) (step 5) takes place by heating under reflux during several hours a mixture containing the compound and 2-iodoxybenzoic acid (or a mixture thereof stabilized with other acids); and the hydrolysis of the compound (VII) (step 6) takes place by treating it with a strong acid, such as p-toluenesulfonic acid or hydrochloric acid or sulfuric acid.

Characteristic of the invention is step 3, the selective reduction of carbonyl in position 17 only of compound (IV), in the presence of a carbonyl in position 11, to form the corresponding 17-alcohol (V). In the formula of compound (V) (as in that of compound (VI)), the stereochemistry of group —OH in position 17 is undefined. Actually, it has been experimentally observed that by operating according to the invention, isomer β is selectively or exclusively obtained in this step even if none of the known techniques is used to induce a particular stereochemistry in this reaction. The stereochemistry at position 17 is in any case immaterial for the process of the invention, since in step 5, the —OH group in position 17 of compound (VI) is oxidized again to the corresponding ketone.

The selective reduction of carbonyl in position 17 only prevents the need of selectively re-oxidizing a possible alcohol group in position 11 and allows the carbonyl group to be in this position, already ready for the subsequent Wittig reaction, which introduces a methylene group in this position.

Such a selective reduction is obtained by using metal hydrides such as sodium borohydride and lithium aluminum hydride in the presence of cerium trichloride; sodium borohydride in the presence of cerium trichloride heptahydrate is preferably used. The reaction temperature is from −10° C. to 40° C., preferably from 0 to 10° C. The reaction time is from 30 minutes to 3 hours, preferably from 1 to 2 hours. The reaction occurs by using as a solvent a mixture between at least two solvents selected from methanol, ethanol, isopropanol, cyclohexanol, ethyl ether, isopropyl ether, tetrahydrofuran, methyltetrahydrofuran, chloroform and methylene chloride, said mixture being such that at least one of the components is an alcohol and at least a second component is other than an alcohol.

The selective reduction of the carbonyl group in position 17 of 18-methyl-estr-5-en-3,11,17-trione 3,3'-acetal (IV) to form the corresponding 17-alcohol (V), i.e. step 3 of the above-described process, is a further object of the present invention.

The process of the invention allows several advantages to be achieved as compared to the prior art. As already mentioned above, compared to the process in U.S. Pat. No. 3,927,046, it avoids the use of chromium(VI)-based reagents; does not require resorting to chromatographic purifications; and compared to the total synthesis method described in the above article by E. J. Corey et al., or to the method in CN 1865276, it greatly reduces the number of process steps, allowing 11-methylene-18-methylestr-4-en-3,17-dione to be obtained starting from 11α-hydroxy-18-methyl-estra-4-en-3,17-dione in just 6 reactions. Moreover, it prevents the need for the reaction of double protection of carbonyls in position 3 and 17 (and the above-mentioned drawbacks related to such a double protection, i.e. the formation of a complex mixture of products due to both the migration of the double bond, from positions 4(5) to positions 5(10) and 5(6), and to the configuration instability caused by the hydroxyl in 11α), and it only requires the use of commonly used reagents and solvents easily available on the market and usable with no particular legislative responsibilities.

The invention will be further described by means of the following examples.

The analytical data given in the examples were obtained under the following conditions:
IR spectra obtained from KBr pellet samples;
NMR spectra recorded on samples dissolved in CDCl$_3$;
mass spectra obtained through electronic impact (EI) or chemical ionization (CI). In the case of chemical ionization (CI), the peaks recorded show a +1 mass compared to the theoretical one.

All the reactions described in the examples are run under an inert atmosphere (nitrogen).

In the examples, the following abbreviations are used:
AcOiPr: isopropyl acetate
DMSO: dimethylsulfoxide
HPTLC: High Performance Thin Layer Chromatography
IBX: 2-iodoxybenzoic acid
iPrO$_2$: isopropyl ether
MePPh$_3$I: methyl triphenylphosphonium iodide
Me-THF: 2-methyl-tetrahydrofuran
MTBE: methylterbuthylether
PTSA: p-toluenesulfonic acid
PySO$_3$: complex pyridine-SO$_3$
SIBX: commercial stabilized mixture of IBX with benzoic acid and isophthalic acid
TEA: triethylamine
TEOF: triethyl orthoformate, HC(OC$_2$H$_5$)$_3$
THF: tetrahydrofuran.

Example 1

Preparation of 18-methyl-estra-4-en-3,11,17-trione, Compound (III)

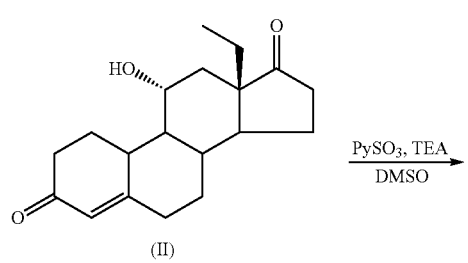

(II)

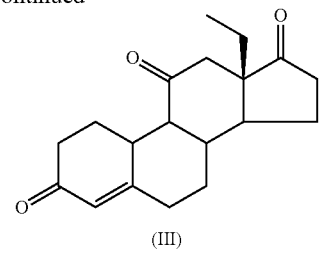

(III)

50 g of compound (II) are dissolved in 125 mL DMSO; 229 mL TEA are then added. Keeping the temperature between 25° C. and 35° C., 79 g of PySO$_3$ dissolved in 225 mL DMSO are added. Exothermy is observed during the addition. Stirring is continued for 3 hours at 25° C.

Reaction check via HPTLC: reaction ended (only a halo is observed, which corresponds to the starting product).

The reaction mixture is transferred to a solution of 375 mL glacial acetic acid in 750 mL water; exothermy (temperature from RT to 40° C.) and formation of a precipitate are observed during the addition. The pH is checked and found to be about 4. The solution is cooled to 0° C. for 1 hour, filtered and dried in stove at T=60° C. for 16 hours, yielding 34.53 g of product. Mother liquor is re-extracted with 500 mL AcOiPr (1 time 300 mL, 2 times 100 mL).

The solvent is distilled under reduced pressure at T=50° C.

150 mL water is added under stirring, observing the formation of a precipitate. The suspension is cooled to T=0° C. stirring for at least 10 minutes. The solid is filtered and dried in stove at T=60° C. for 16 hours, yielding 8.93 g of product.

260 mL isopropyl alcohol (6 volumes) is added to the crude product (two combined jets). The mixture is heated under reflux up to complete dissolution and it is then cooled to 0° C. for at least 1 hour. The solid is filtered and dried in stove at T=60° C., yielding 40.21 g of compound (III).

Compound (II) Analysis
IR (KBr): 3473 cm$^{-1}$; 1732 cm$^{-1}$, 1647 cm$^{-1}$; 1620 cm$^1$
Mass (EI):=M$^+$=302; M$^+$–H$_2$O=284
Molecular weight C$_{19}$H$_{26}$O$_3$=302

Compound (III) Analysis
IR (KBr): 1.737 cm$^{-1}$; 1.703 cm$^{-1}$; 1.662 cm$^{-1}$; 1.608 cm$^{-1}$
Mass (CI): M$^+$+1=301; M$^+$+1–H$_2$O: M$^+$+1–2H$_2$O=265
Molecular weight C$_{19}$H$_{24}$O$_3$=300

Example 2

Preparation of the Acetal of Formula (IV), where R1+R2=—CH$_2$—CH$_2$—

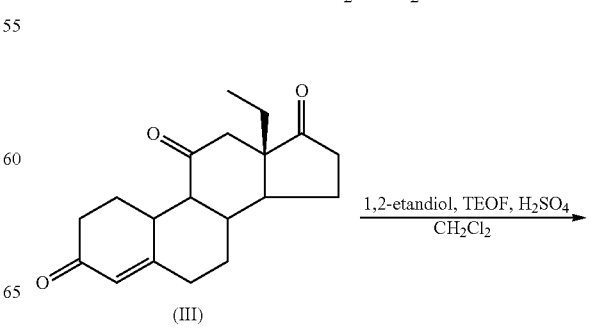

(III)

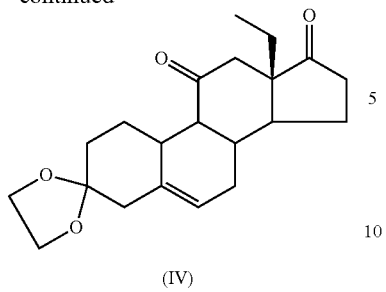

(IV)

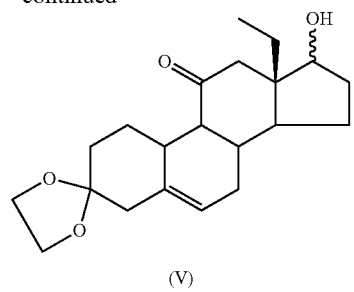

(V)

38 g of intermediate product (III) are dissolved in 1900 mL methylene chloride. The following is sequentially added: 37.6 mL 1,2-etandiol, 38 mL triethyl orthoformate and 1.23 mL 98% $H_2SO_4$. Keeping the temperature between 18 and 20° C., it is stirred for 1.5 hours.

Reaction check via HPTLC: reaction ended.

The following is sequentially added to the reaction solution: 0.9 mL pyridine, 76 mL 10% aqueous solution of $NaHCO_3$, 380 mL water. The pH of the aqueous phase is measured and found equal to 7. The biphasic mixture is vigorously stirred for at least 20 minutes. The phases are separated. The organic phase is washed with water (304 mL twice).

The organic phase is concentrated under reduced pressure at a temperature of about 45° C. The resulting solid is completely dissolved in 75 mL methylene chloride. 70 mL MTBE is added. The methylene chloride is distilled at atmospheric pressure at 55° C. The suspension is cooled to T=0° C. stirring for at least 1 hour. The solid is filtered and washed with cold MTBE (7 mL twice).

It is dried in stove at reduced P and T=60° C. for 16 hours, yielding 33.57 g acetal (IV). Mother liquor is concentrated at reduced pressure at 45° C., yielding 13.5 g of a semi-solid oily residue. 10 mL MTBE is added, observing the formation of a precipitate. It is cooled to 0° C. for 30 minutes.

The solid is filtered and washed with cold MTBE (2 mL twice) and dried at 50° C. for 16 hours, yielding an additional 3.45 g acetal (IV).

Compound (IV) Analysis:

IR (KBr): 1728 $cm^{-1}$; 1699 $cm^{-1}$

Mass (CI): $M^+ + 1 = 345$; $M^+ + 1 - H_2O = 327$

Molecular weight $C_{21}H_{28}O_4 = 344$

NMR ($CDCl_3$): 5.46 ppm (1H, d, H6)

Example 3

Preparation of 17-hydroxy-18-methyl-estr-5-en-3,11-dione 3,3'-acetal (V)

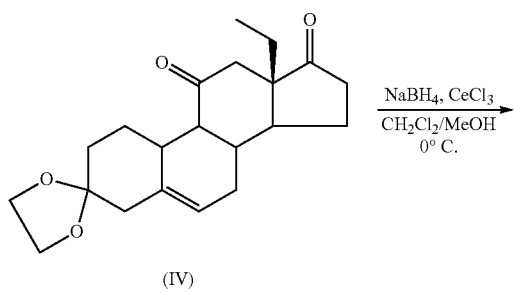

(IV)

32 g of compound (IV) are dissolved in 656 mL methylene chloride. 656 mL methanol and 31.2 g $CeCl_3.7H_2O$ are added and the solution is cooled to 0° C. 2.24 g $NaBH_4$ are then added in 4 portions over 20 minutes, observing a light exothermy (the temperature of the reaction mixture reaches about 5-10° C.) and gas generation. A clouding of the reaction mixture is observed. Stirring is continued for 1 hour at 0° C.

Reaction check in HPTLC: reaction ended, residual compound (IV) less than 2%.

A solution of 1.6 mL acetic acid in 819 mL water is added to the reaction mixture; the pH is equal to 6.

The solvent is distilled under reduced pressure at 45° C., observing the formation of a precipitate. It is cooled to 0° C. for at least one hour. It is filtered and washed with water (160 mL three times). The solid is stirred with 128 mL toluene (the solid does not dissolve completely). The solvent is evaporated under reduced pressure at 50° C., yielding 31.73 g of intermediate compound (V).

Compound (V) Analysis:

IR (KBr): 3539 $cm^{-1}$; 1704 $cm^{-1}$; 1670 $cm^{-1}$

Mass (CI): $M^+ + 1 = 347$; $M^+ + 1 - H_2O = 329$

Molecular weight $C_{21}H_{30}O_4 = 346$

NMR ($CDCl_3$): 5.46 ppm (1H, d, H6); 4.04-3.90 ppm (5H, m, H17 and H acetal); 2.91 ppm (1H, d); 2.44-0.90 ppm (23H, Σmultiplets).

Example 4

Preparation of 17-hydroxy-18-methyl-estr-5-en-3,11-dione 3,3'-acetal (V)

The test in example 3 is repeated starting from 30 g of compound (IV) rather than 32 g and deducting the amounts of all reagents to a corresponding extent.

Unlike example 3, after the addition of $NaBH_4$, the stirring at 0° C. is kept for 2 hours, observing an amount of unreacted compound (IV) less than 0.3% at the check in HPLC; moreover, after filtering and washing with water 3 times (150 mL), in this case the product is not stirred with toluene but directly dried in a stove at 50° C., yielding 27.4 g of compound (V).

The analyses of the compound give results corresponding to the product in example 3.

Example 5

Preparation of 17-hydroxy-18-methyl-estr-5-en-3,11-dione 3,3'-acetal (V)

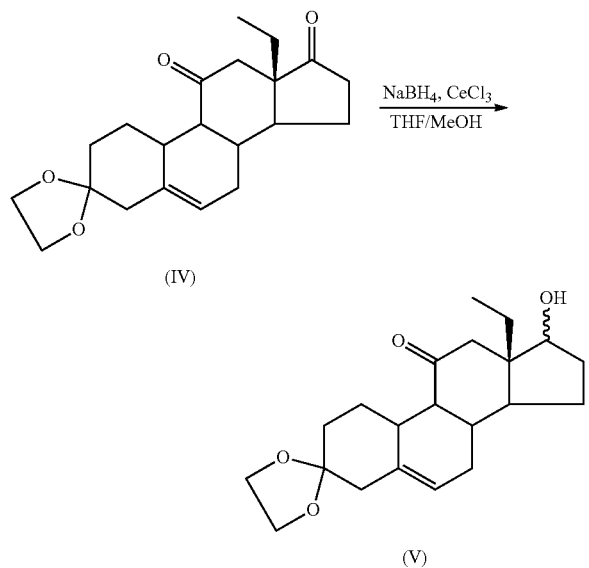

10 g of compound (IV) are suspended in 350 mL methanol and 150 mL THF. 11.5 g CeCl₃.7H₂O and then 1.1 g NaBH₄ are added in 5 portions over 10 minutes. The mixture is kept under stirring at 20-25° C. for 1 hour.

Reaction check in HPTLC: residual compound (IV) less than 2%.

A solution of 1 L water and 5 mL acetic acid is added to the reaction mixture. The pH is adjusted to 6-7 with a basic aqueous solution. The solvent is distilled under reduced pressure at 45° C., after which it is cooled to 0° C. for at least one hour. It is filtered and washed with water (150 mL three times).

It is dried in a stove at 60° C., yielding 9.2 g of compound (V).

The analyses of the compound give results corresponding to the product in example 3.

Example 6

Preparation of 17-hydroxy-18-methyl-estr-5-en-3,11-dione 3,3'-acetal (V)

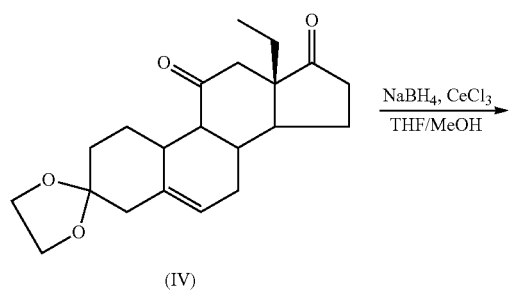

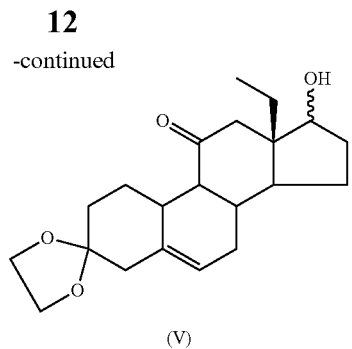

10 g of compound (IV) are suspended in 50 mL methanol and 25 mL THF. 11.5 g CeCl₃.7H₂O and then 1.1 g NaBH₄ are added in 6 portions over 20 minutes. The temperature of the reaction mixture rises to more than 35° C.

Stirring is continued without cooling and a check is made in HPTLC after 2 h and 30 minutes; the check still shows the presence of residual compound (IV). Two additional portions of NaBH₄ (0.4 g and 0.3 g) are added over 1 h.

Reaction check in HPTLC after 1 h: residual compound (IV) not detectable.

100 mL water is added to the reaction mixture. The solvent is distilled under reduced pressure at 45° C., after which it is cooled to 0° C. for at least one hour. It is filtered and washed with water (100 mL three times). It is dried in a stove at 60° C., yielding 9.1 g of compound (V).

The TLC check shows the largely minority presence of a second product with Rf lower than the intermediate product (V).

Example 7

Preparation of 17-hydroxy-18-methyl-estr-5-en-3,11-dione 3,3'-acetal (V)

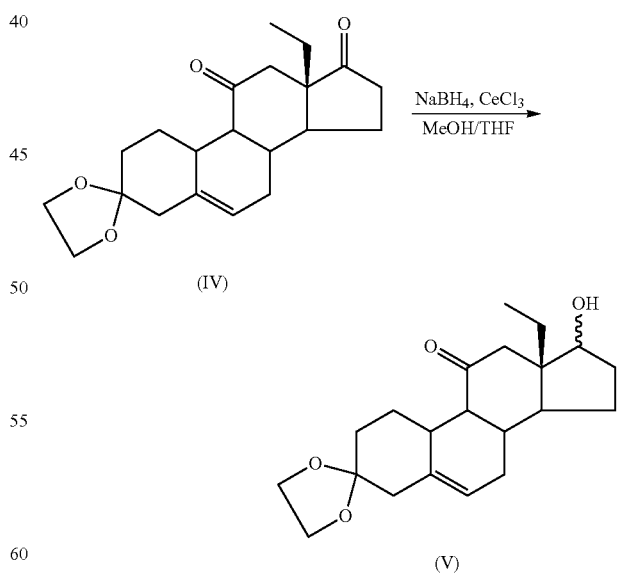

50 g of compound (IV) are suspended in 2.5 L mixture of methanol/THF 2:1 v/v at 20-25° C. 58.5 g CeCl₃.7H₂O and 5.5 g NaBH₄ are added in portions over about 15 minutes. The temperature rises spontaneously to 30° C. Stirring is carried out for 1 hour.

Reaction check in HPLC: reaction ended, residual compound (IV) less than 1%.

Stirring is continued for 1 h repeating the HPLC check. A solution of 28 mL acetic acid in 3.5 L water is added to the reaction mixture, after which extraction is carried out with ethyl acetate (1 L three times). The solvent is distilled under reduced pressure at 45° C., yielding 54 g of crude compound (V) (yellow oil).

50 g of crude compound (V) are dissolved in 40 mL methylene chloride. 60 mL heptane is added and methylene chloride is distilled at atmospheric pressure. It is cooled to 0-5° C., filtering the resulting solid. After drying at 50° C. for 12 hours, 40.8 g of compound (V) are obtained.

The analyses of the compound give results corresponding to the product in example 3.

Example 8

Preparation of 17-hydroxy-18-methyl-estr-5-en-3,11-dione 3,3'-acetal (V)

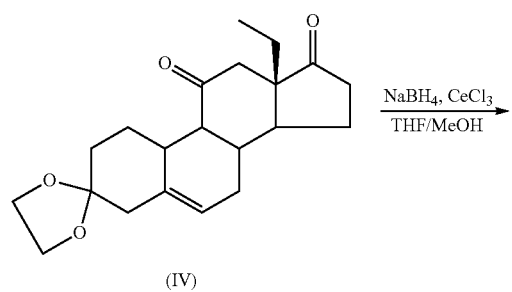

(IV)

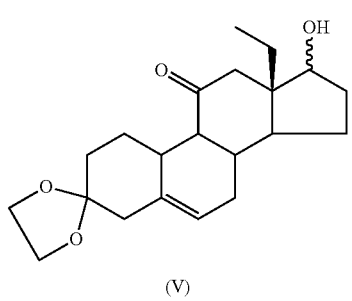

(V)

7 g of compound (IV) are suspended in a solution obtained by mixing 167 mL THF and 233 mL methanol at T=20-22° C. 8.19 g $CeCl_3 \cdot 7H_2O$ and 770 mg $NaBH_4$ are added. By spontaneous exothermy, the reaction mixture reaches 27° C. Stirring is continued for 45 minutes, letting the temperature drop to 20-25° C.

Reaction check in HPTLC: residual compound (IV) not detectable.

A solution of 4 mL acetic acid in 500 mL water is added to the reaction mixture. Extraction is carried out with ethyl acetate (100 mL three times). After distillation of the solvent under reduced pressure at 45° C., 6.75 g of compound (V) are obtained.

The analyses of the compound give results corresponding to the product in example 3.

Example 9

Preparation of 17-hydroxy-18-methyl-estr-5-en-3,11-dione 3,3'-acetal (V)

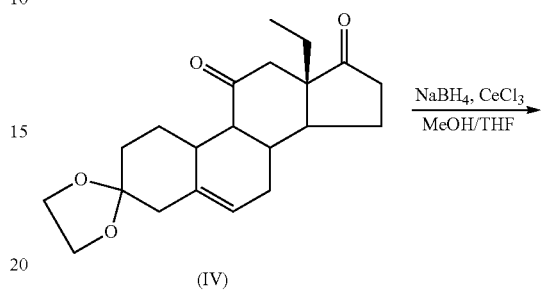

(IV)

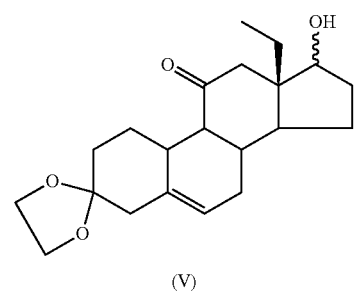

(V)

7.47 g of compound (IV) are suspended in 350 mL of a solution of methanol-THF 2:1 v/v at T=20-22° C. 8.47 g $CeCl_3 \cdot 7H_2O$ and 830 mg $NaBH_4$ are added. The reaction mixture reaches 28° C. by spontaneous exothermy. Stirring is continued for 60 minutes letting the temperature drop to 20-25° C.

Reaction check in HPTLC: residual compound (IV) not detectable.

A solution of 4 mL acetic acid in 500 mL water is added to the reaction mixture. Extraction is carried out with ethyl acetate (100 mL three times).

After distillation of the solvent under reduced pressure at 45° C., 6.9 g of compound (V) are obtained.

The analyses of the compound give results corresponding to the product in example 3.

Example 10

Preparation of 17-hydroxy-11-methylene-18-methyl-estra-5-en-3-one-3,3' acetal (VI)

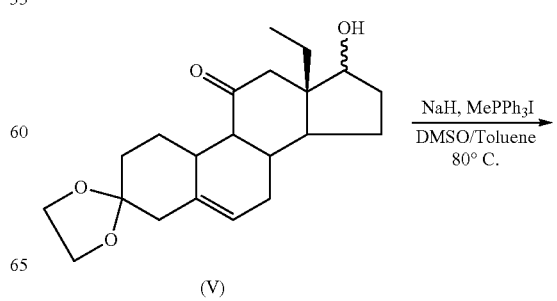

(V)

-continued

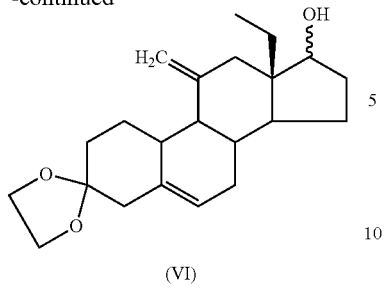

(VI)

96.38 g MePPh₃I are dissolved in 250 mL DMSO. 5.55 g NaH are added (60%). Gas generation and a light exothermy are observed (the mixture reaches about 30° C.). It is heated to 80° C. and the reaction mixture is kept at this temperature for 1.5 hours. Complete dissolution is observed. A suspension of 25 g of compound (V) in 120 mL toluene is added. Stirring is continued for 3 hours at 80° C.

Reaction check in HPTLC: reaction ended.

The reaction mixture is cooled to 25° C. and transferred to 870 mL water. Gas generation and a light exothermy are observed (the mixture reaches about 30° C.). Extraction is carried out with toluene (90 mL four times). The organic phase is washed with water (90 mL twice).

Mother liquor is checked by HPTLC. The solvent is distilled under reduced pressure at 45° C. The residue is stirred with 230 mL acetone and distilled under reduced pressure at 45° C. The oily residue is stirred with an additional 230 mL acetone. It is slowly dripped in 870 mL water. The acetone is distilled under reduced pressure at 45° C., after which it is cooled to 0° C. for 1 hour. The solid is filtered and stirred with 200 mL acetone. The mixture is heated under reflux up to complete dissolution and cooled to 0° C. for 1 hour. The solid is filtered and washed with cold acetone (5 mL twice). It is dried in a stove at 45° C., obtaining 20.04 g of compound (VI).

Compound (VI) Analysis:

IR (KBr): 3514 cm$^{-1}$

Mass spectrum (CI): M$^+$+1=345; M$^+$+1−H$_2$O=327

Molecular weight C$_{22}$H$_{32}$O$_3$=344

NMR (CDCl$_3$, 500 MHz): 5.50 ppm, (1H, d, H$_6$); 4.97 (1H, s, H 11 methylene); and 4.80 ppm (1H, s, H 11 methylene); 4.01-3.96 ppm (4H, m, H acetal); 3.74 ppm (1H, t, H$_{17}$); 2.77 ppm (1H, d); 2.33-1.0 ppm (23H, Σm).

Example 11

Preparation of Compound 11-methylene-18-methyl-estr-5-en-3,17-dione-3,3' acetal (VII)

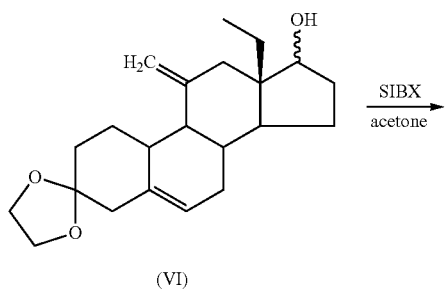

(VI)

-continued

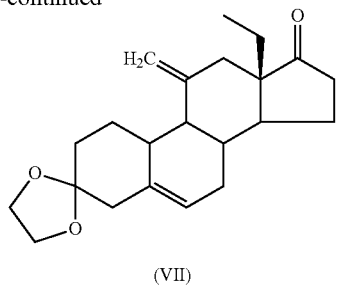

(VII)

11 g of compound (VI) are dissolved in 220 mL acetone. 23.76 g SIBX are added: the reaction mixture remains cloudy. It is heated under reflux (56° C.) for 3 hours.

Reaction check in TLC: reaction ended.

The reaction mixture is cooled to 20° C., 280 mL of an aqueous solution of NaOH 0.6 M and 220 mL water are added and the pH is checked and found to be about 8. It is cooled to 0° C. for 1 hour. The solid is filtered and washed with water (16.5 mL twice). The crude product is suspended in 22 mL methylene chloride and stirred at 25° C. for 30 minutes. It if filtered and washed with methylene chloride (10 mL twice). It is distilled at atmospheric pressure up to a residue of about 22 mL. 88 mL MTBE are added and concentrated to a residue of about 44 mL; the formation of a precipitate is observed. An additional 88 mL MTBE is added and concentrated to a residue of about 44 mL. It is cooled to 0° C. for 1 hour and filtered. It is washed with cold MTBE (5.5 mL twice).

It is dried at 50° C. under reduced pressure, obtaining 7.73 g of compound (VII). Mother liquor is concentrated again to about half the volume. It is cooled to 0° C. for 1 hour. The solid is filtered and washed with 2 mL cold MTBE. It is dried under reduced pressure at 50° C., yielding an additional 0.84 g of compound (VII).

Compound (VII) Analysis:

IR (KBr): 1724 cm$^{-1}$

Mass spectrum (CI): M$^+$+1=343; M$^+$+1−H$_2$O=325

Molecular weight C$_{22}$H$_{30}$O$_3$=342

NMR (CDCl$_3$, 500 MHz): absence of peaks attributable to the proton in position 17.

Example 12

Preparation of Compound 11-methylene-18-methyl-estr-5-en-3,17-dione-3,3' acetal (VII)

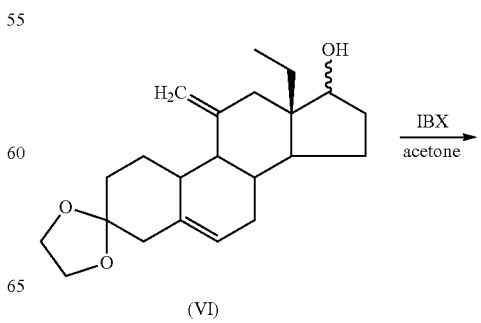

(VI)

-continued

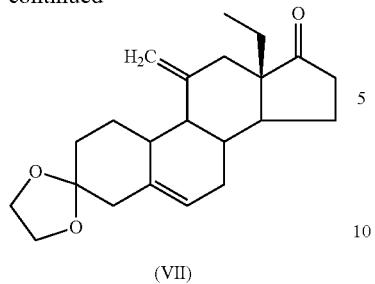

(VII)

-continued

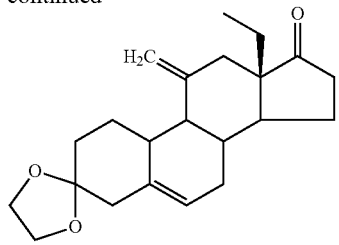

(VII)

20 g of compound (VI) are dissolved in 300 mL acetone. 21.16 g IBX are added. The reaction mixture remains cloudy. It is heated under reflux (56° C.) for 6 hours.

Reaction check in HPTLC: reaction ended.

The reaction mixture is cooled to 20° C. 150 mL of an aqueous solution of NaOH 0.6 M and 200 mL water are added and the pH is checked and found to be about 11. It is cooled to 0° C. for at least 30 minutes. The solid is filtered and washed with water (30 mL twice). It is dried in a stove at 6° C., obtaining 19.58 g of crude compound (VII), which are dissolved in 40 mL methylene chloride. 160 mL iPr$_2$O are added. It is distilled at atmospheric pressure up to a residue of about 80 mL. It is cooled to 0° C. for at least 30 minutes and the solid is filtered. It is washed with cold iPr$_2$O (10 mL twice).

It is dried at 50° C. under reduced pressure, obtaining 15.5 g of compound (VII), which are stirred with 40 mL methylene chloride. It is filtered on a dicalite panel and the solvent is distilled under reduced pressure, obtaining 15.24 g of compound (VII) as a white solid.

The analyses of the compound give results corresponding to the product in example 11.

19.5 g of compound (VI) are dissolved in 292 mL acetone. 20.6 g IBX are added: the reaction mixture remains cloudy. It is heated under reflux (56° C.) for 6 hours.

Reaction check in HPTLC: reaction ended.

The reaction mixture is cooled to 20° C. 146 mL of an aqueous solution of NaOH 0.6 M and 195 mL water are added and the pH is checked and found to be about 9. It is cooled to 0° C. for 1 hour. The solid is filtered and washed with water (29 mL twice). It is dried in a stove at 60° C. for 16 hours, obtaining 20.77 g of compound (VII). The crude product is suspended in 40 mL methylene chloride and stirred at 25° C. for 30 minutes. It if filtered on dicalite, washing with methylene chloride (10 mL twice). It is distilled at atmospheric pressure up to a residue of about 40 mL. 160 mL MTBE are added and concentrated to a residue of about 80 mL. The formation of a precipitate is observed. It is cooled to 0° C. for 1 hour and filtered. It is washed with cold MTBE (2×10 mL). It is dried at 50° C. under reduced pressure, yielding 11.36 g of compound (VII).

Mother liquor is concentrated again to dryness, obtaining 6.82 g residue. 20 mL MTBE (3 volumes) are added and stirred at 25° C. for 30 minutes. It is cooled to 0° C. for 1 hour. The solid is filtered and washed with 5 mL cold MTBE. It is dried at 50° C. under reduced pressure, obtaining an additional 4.25 g of compound (VII).

The analyses of the compound give results corresponding to the product in example 11.

Example 13

Preparation of Compound 11-methylene-18-methyl-estr-5-en-3,17-dione-3,3' acetal (VII)

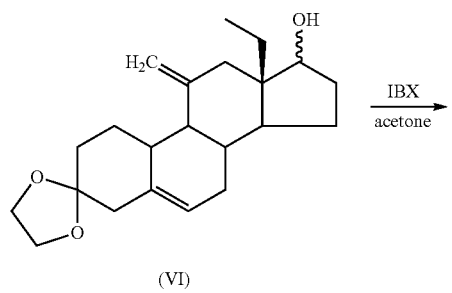

(VI)

Example 14

Preparation of Compound 11-methylene-18-methyl-estr-4-en-3,17-dione-3,3' acetal (VII)

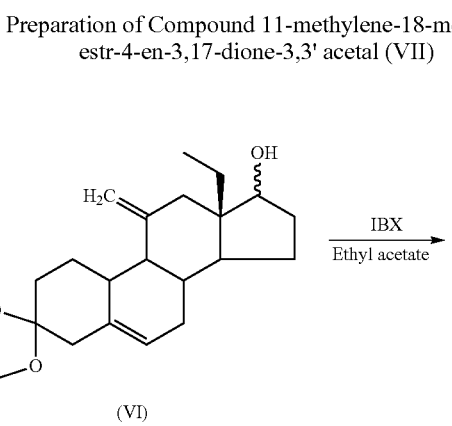

(VI)

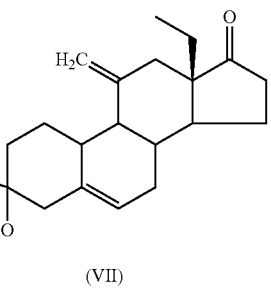

(VII)

1 g of compound (VI) is dissolved in 30 mL ethyl acetate. 4 g IBX are added and heated under reflux for 3 h.

Reaction check in HPTLC: reaction ended.

The reaction mixture is cooled to 0-5° C. The solid is filtered and the organic phase (containing the product) is concentrated under reduced pressure. After drying, the crude product is crystallized from a mixture of methylene chloride-isopropyl ether.

It is dried at 50° C. under reduced pressure, yielding 0.7 g of compound (VII).

Example 15

Preparation of Compound
11-methylene-18-methyl-estr-4-en-3,17-dione (I)

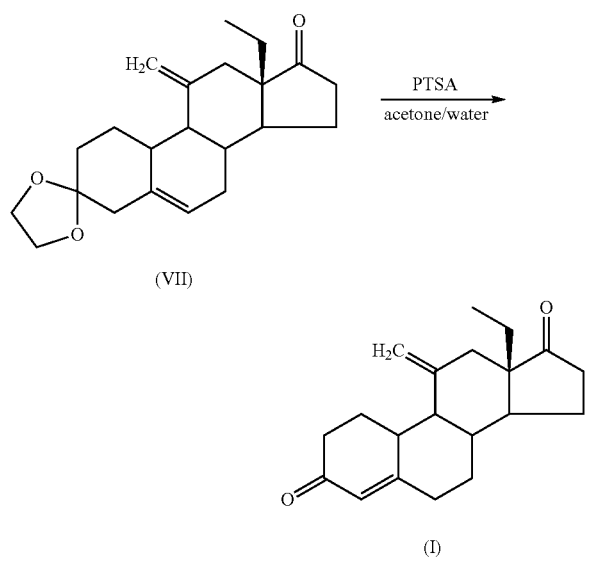

5.5 g of compound (VII) are suspended under nitrogen in 110 mL acetone.

1.42 g PTSA and 1.1 mL water are then added. It is heated to 35° C. and a complete dissolution is observed. The temperature is brought back to 25° C. and the mixture is kept under stirring for 3 hours.

Reaction check via TLC: compound (VII) not detectable.

2.84 g NaHCO₃ dissolved in 86 mL water are then added to the reaction mixture; the pH is measured and found to be equal to 7. The acetone is distilled under reduced pressure, the mixture is cooled to 0° C. for 30 minutes, the solid is filtered and washed with 16.5 mL water.

It is dried at 55° C. under reduced pressure for 16 hours, obtaining 4.59 g of the desired compound (I). A sample of product, purified for analytical purposes by silica gel chromatography, shows NMR (CDCl₃) and mass (EI) spectra according to the literature data.

Example 16

Comparative

This example, not according to the invention, relates to a reduction reaction of compound (IV) without using cerium trichloride.

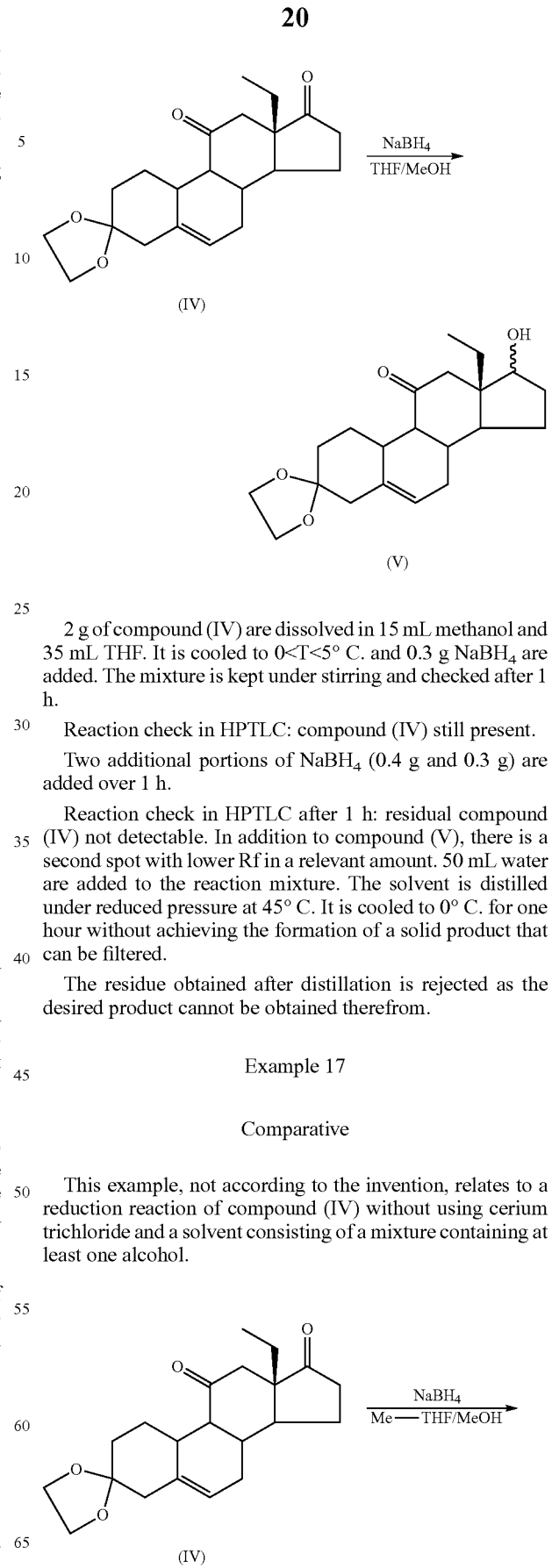

2 g of compound (IV) are dissolved in 15 mL methanol and 35 mL THF. It is cooled to 0<T<5° C. and 0.3 g NaBH₄ are added. The mixture is kept under stirring and checked after 1 h.

Reaction check in HPTLC: compound (IV) still present.

Two additional portions of NaBH₄ (0.4 g and 0.3 g) are added over 1 h.

Reaction check in HPTLC after 1 h: residual compound (IV) not detectable. In addition to compound (V), there is a second spot with lower Rf in a relevant amount. 50 mL water are added to the reaction mixture. The solvent is distilled under reduced pressure at 45° C. It is cooled to 0° C. for one hour without achieving the formation of a solid product that can be filtered.

The residue obtained after distillation is rejected as the desired product cannot be obtained therefrom.

Example 17

Comparative

This example, not according to the invention, relates to a reduction reaction of compound (IV) without using cerium trichloride and a solvent consisting of a mixture containing at least one alcohol.

-continued

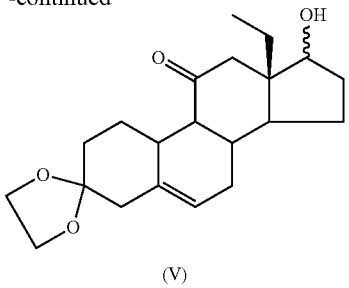

(V)

2 g of compound (IV) are suspended in 30 mL Me-THF and 15 mL methanol. It is cooled to 0<T<5° C. and 0.22 g NaBH$_4$ are added. The mixture is kept under stirring and checked after 1 h.

Reaction check in HPTLC: prevalent compound (IV).

Two additional portions of 0.1 g NaBH$_4$ are added.

Reaction check in HPTLC after 24 h: residual compound (IV) not detectable.

In addition to compound (V), there is a second spot in a prevalent amount with lower Rf.

The reaction mixture is eliminated.

Example 18

Comparative

This example, not according to the invention, relates to a reduction reaction of compound (IV) without using cerium trichloride.

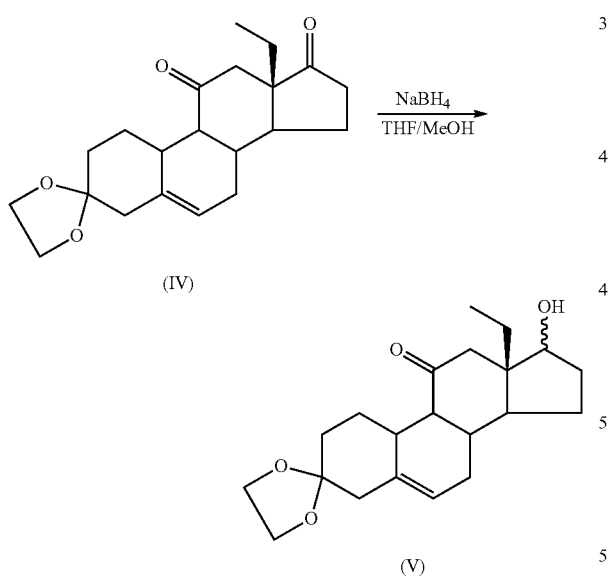

1 g of compound (IV) is dissolved in 50 mL of a solution of methanol:THF 2:1 v/v. It is cooled to 0<T<5° C. and 110 mg NaBH$_4$ are added. The mixture is kept under stirring for 16 h at a temperature from −10 to 0° C.

Reaction check in HPTLC: residual compound (IV) detectable.

An additional portion of NaBH$_4$ (110 mg) is added and the mixture is brought to 20-25° C.

Reaction check in HPTLC after 1 h: residual compound (IV) detectable.

An additional portion of NaBH$_4$ (110 mg) is added and the mixture is kept at 20-25° C. for an additional 16 h.

Reaction check in HPTLC: compound (IV) detectable.

A solution of 1 mL acetic acid in 180 mL water is added to the reaction mixture. Extraction is carried out with ethyl acetate (50 mL three times). After distillation of the solvent under reduced pressure at 45° C., are obtained 980 g of a mixture which, at a TLC check, shows the presence of three main spots.

The sample is subjected to silica gel flash column chromatography with a medium pressure, automated system, thus separating the reaction products. The purpose of the separation is purely analytical, whereby the fractions corresponding to the central part of the peaks are collected.

The product in lower amount (52 mg) corresponds to the starting compound (IV).

The other two products show a mass spectrum (EI) according to the reduction product of a single carbonyl group, i.e. M$^+$+1=347; M$^+$+1−H$_2$O=329 (C$_{21}$H$_{30}$O$_4$=346).

On the other hand, the NMR spectra (CDCl$_3$, 500 MHz) show a clear difference in the chemical shift ascribable to the proton in position 17. The main product (450 mg) does not show the signal ascribable to the proton in position 17 which is covered by the signals of acetal (4.04-3.90 ppm, m, 5H), while the other one (138 mg) clearly expresses it (4.26 ppm, s, 1 h, H17) separated from the signals ascribable to the protons of acetal (3.87-4.00, m, 4H).

These assays show that, by operating in the absence of the cerium compound, a mixture of products is obtained which still contains a minority part of the starting compound (IV), and a mixture of two isomer alcohols with configuration α and β in position 17 (corresponding to formula (V)).

The invention claimed is:

1. A method for the selective reduction of the carbonyl group in position 17 of 18-methyl-estr-5-en-3,11,17-trione 3,3'-acetal (IV)

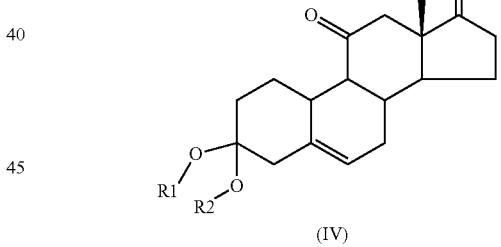

to form 17-hydroxy-18-methyl-estr-5-en-3,11-dione 3,3'-acetal (V)

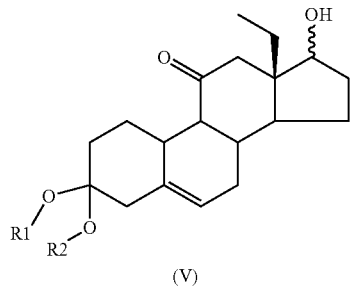

wherein R1 and R2 can be either separate alkyl radicals C1-C3 equal to each other, or they can form a unique bidentate alkyl radical C2-C4, and the symbol ∼∼∼ indicates that the —OH group may have configuration α or β, said reduction carried out using a metal hydride in the presence of cerium trichloride, operating at a temperature comprised between −10 and 40° C. during a time comprised between 30 minutes and 3 hours, in a solvent consisting of a mixture between at least an alcohol selected among methanol, ethanol, isopropanol and cyclohexanol, and at least a second solvent selected among ethyl ether, isopropyl ether, tetrahydrofuran, methyltetrahydrofuran, chloroform and methylene chloride.

2. The process according to claim 1, wherein said metal hydride is selected between sodium borohydride and lithium aluminum hydride.

3. The process according to claim 2, wherein said metal hydride is sodium borohydride in the presence of cerium trichloride heptahydrate.

* * * * *